US00RE43389E

(19) United States
(12) Reissued Patent
Helftenbein

(10) Patent Number: US RE43,389 E
(45) **Date of Reissued Patent: *May 15, 2012**

(54) VESSEL FOR BLOOD SAMPLING

(75) Inventor: Elke Helftenbein, Stuttgart (DE)

(73) Assignee: PreAnalytix GmbH, Hombrechtikon (CH)

( * ) Notice: This patent is subject to a terminal disclaimer.

(21) Appl. No.: 11/506,164

(22) Filed: Aug. 17, 2006

Related U.S. Patent Documents

Reissue of:
(64) Patent No.: 6,776,959
Issued: Aug. 17, 2004
Appl. No.: 09/762,643
PCT Filed: Aug. 12, 1999
PCT No.: PCT/EP99/05857
§ 371 (c)(1),
(2), (4) Date: May 18, 2001
PCT Pub. No.: WO00/09746
PCT Pub. Date: Feb. 24, 2000

(30) Foreign Application Priority Data

Aug. 12, 1998 (DE) ..... 198 36 559

(51) Int. Cl.

| | |
|---|---|
| ***C12Q 1/68*** | (2006.01) |
| ***C07H 21/00*** | (2006.01) |
| ***G01N 1/00*** | (2006.01) |
| ***G01N 21/00*** | (2006.01) |
| ***C12M 1/00*** | (2006.01) |
| ***C12M 3/00*** | (2006.01) |
| ***A61B 5/00*** | (2006.01) |
| ***A01N 1/02*** | (2006.01) |
| ***B01L 3/00*** | (2006.01) |

(52) U.S. Cl. ..... 435/6.1; 536/25.4; 436/174; 436/176; 435/2; 435/4; 435/6; 435/283.1; 435/287.2; 600/573; 600/577; 422/50; 422/58; 422/102

(58) Field of Classification Search ..... 435/6; 536/23.1, 536/24.3, 25.4, 22.1, 25.41; 422/102; 436/8, 436/176
See application file for complete search history.

(56) References Cited

U.S. PATENT DOCUMENTS

| | | | | |
|---|---|---|---|---|
| 2,460,641 | A * | 2/1949 | Kleiner | 600/577 |
| 3,847,738 | A | 11/1974 | Brake et al. | |
| 3,879,295 | A * | 4/1975 | Glover et al. | 210/516 |
| 4,040,785 | A | 8/1977 | Kim et al. | |
| 4,311,482 | A | 1/1982 | Workman, Jr. et al. | |
| 4,336,880 | A * | 6/1982 | Mehl | 206/524.4 |
| 4,342,566 | A | 8/1982 | Theofilopoulos et al. | |
| 4,424,279 | A * | 1/1984 | Bohn et al. | 436/534 |
| 4,529,614 | A | 7/1985 | Burns | |
| 4,558,142 | A * | 12/1985 | Holland et al. | 549/465 |
| 4,808,449 | A | 2/1989 | McAlister | |
| 4,812,310 | A | 3/1989 | Sato et al. | |
| 4,843,155 | A | 6/1989 | Chomczynski | |
| 4,882,282 | A * | 11/1989 | Anderson et al. | 435/252.3 |
| 4,931,543 | A | 6/1990 | Halenbeck et al. | |
| 4,935,342 | A | 6/1990 | Seligson et al. | |
| 4,938,758 | A | 7/1990 | Al-Sioufi | |
| 5,010,183 | A | 4/1991 | Macfarlane | |
| 5,019,243 | A * | 5/1991 | McEwen et al. | 210/94 |
| 5,023,323 | A | 6/1991 | Ho | |
| 5,030,341 | A * | 7/1991 | McEwen et al. | 210/94 |
| 5,032,398 | A * | 7/1991 | Kaslow | 424/240.1 |
| 5,046,509 | A * | 9/1991 | Kater | 600/577 |
| 5,073,341 | A | 12/1991 | Hargreaves | |
| 5,215,892 | A * | 6/1993 | Kishimoto et al. | 435/69.1 |
| 5,234,809 | A | 8/1993 | Boom et al. | |
| 5,300,635 | A | 4/1994 | Macfarlane | |
| 5,308,506 | A * | 5/1994 | McEwen et al. | 210/745 |
| 5,346,994 | A | 9/1994 | Chomczynski | |
| 5,354,483 | A * | 10/1994 | Furse | 210/789 |
| 5,380,664 | A | 1/1995 | Carver et al. | |
| 5,456,885 | A | 10/1995 | Coleman et al. | |
| 5,459,253 | A | 10/1995 | Wolin et al. | |
| 5,541,058 | A * | 7/1996 | Kreider et al. | 435/5 |
| 5,545,529 | A | 8/1996 | Costa et al. | |
| 5,610,287 | A | 3/1997 | Nikiforov et al. | |
| 5,620,852 | A | 4/1997 | Lin et al. | |
| 5,637,687 | A | 6/1997 | Wiggins | |
| 5,654,179 | A | 8/1997 | Lin | |
| 5,663,048 | A * | 9/1997 | Winkfein et al. | 435/6 |
| 5,667,963 | A | 9/1997 | Smith et al. | |
| 5,702,884 | A | 12/1997 | Ekeze et al. | |
| 5,728,822 | A | 3/1998 | Macfarlane | |
| 5,744,520 | A | 4/1998 | Kmiecik-Lawrynowicz et al. | |
| 5,747,663 | A | 5/1998 | Colpan et al. | |
| 5,763,199 | A * | 6/1998 | Coller | 435/7.21 |
| 5,777,099 | A | 7/1998 | Mehra | |
| 5,779,983 | A | 7/1998 | Dufresne et al. | |
| 5,792,651 | A | 8/1998 | Colpan et al. | |
| 5,849,517 | A | 12/1998 | Ryan | |
| 5,860,937 | A * | 1/1999 | Cohen | 600/576 |
| 5,882,318 | A * | 3/1999 | Boyde | 600/595 |
| 5,891,736 | A | 4/1999 | Chapoteau et al. | |
| 5,906,744 | A | 5/1999 | Carroll et al. | |

(Continued)

FOREIGN PATENT DOCUMENTS

| | | |
|---|---|---|
| EP | 0 554 034 | 8/1993 |

(Continued)

OTHER PUBLICATIONS

Lozano et al., Virus Research 27 : 37-53 (1993).*
MacDonald et al. Isolation of RNA using Guanidinium Salts. Methods in Enzymology 152 : 219-227 (1987).*
Lozano et al. A Simple nucleic acid amplification assay for the rapid detection of Junin virus in whole blood samples. Virus Research 27 : 37-53 (1993).*
Guanidinium Thiocyanate, Materials Safety Data Sheet, pp. 1-5.*
Brossart et al., Cancer Research 55 : 4065-4068 (1995).*
Brossart et al., J. of Invest. Derm. 101:887-889 (1993).*

(Continued)

*Primary Examiner* — Ethan C Whisenant

(57) ABSTRACT

The present invention relates to a vessel for withdrawing blood, the vessel containing a solution which comprises a guanidinium salt, a buffer substance, a reducing agent, and/or a detergent as components. The vessel is particularly suited for withdrawing blood which is to be analyzed with respect to nucleic acids.

155 Claims, 8 Drawing Sheets

U.S. PATENT DOCUMENTS

Figure 1:
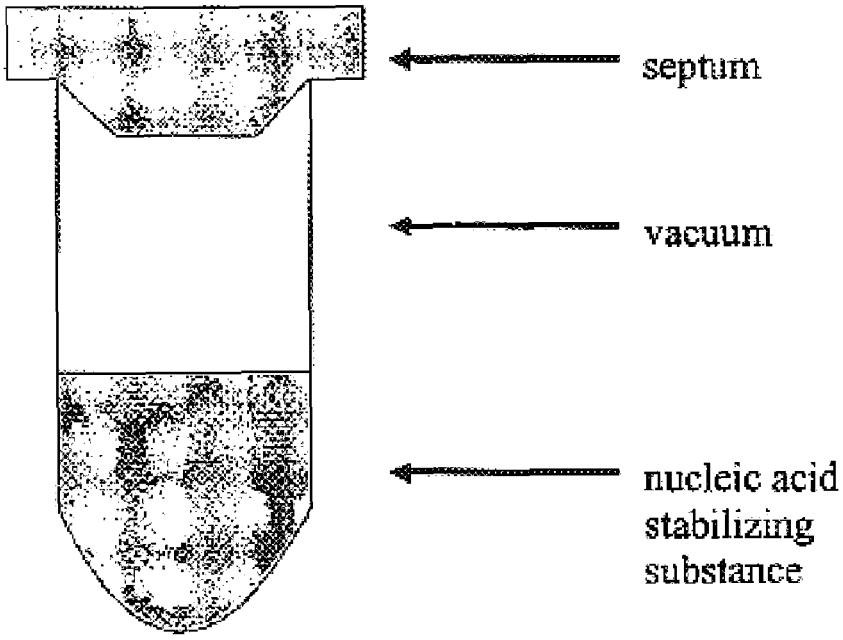

| | | | | |
|---|---|---|---|---|
| 5,932,422 | A | 8/1999 | Shyjan et al. | |
| 5,939,259 | A | 8/1999 | Harvey et al. | |
| 5,942,191 | A * | 8/1999 | Conway | 422/550 |
| 5,958,677 | A * | 9/1999 | Lee et al. | 435/5 |
| 5,968,620 | A * | 10/1999 | Harvey et al. | 428/35.9 |
| 5,985,572 | A | 11/1999 | Macfarlane | |
| 5,989,431 | A | 11/1999 | Evans et al. | |
| 5,990,301 | A | 11/1999 | Colpan et al. | |
| 5,998,601 | A * | 12/1999 | Murtaugh et al. | 536/23.72 |
| 6,020,186 | A | 2/2000 | Henco et al. | |
| 6,027,886 | A | 2/2000 | Leying et al. | |
| 6,037,465 | A | 3/2000 | Hillebrand et al. | |
| 6,043,032 | A | 3/2000 | Yamagishi | |
| 6,102,894 | A * | 8/2000 | Dysarz | 604/110 |
| 6,111,096 | A * | 8/2000 | Laugharn et al. | 204/601 |
| 6,114,108 | A | 9/2000 | Budowsky | |
| 6,168,922 | B1 | 1/2001 | Harvey et al. | |
| 6,218,531 | B1 | 4/2001 | Ekenberg | |
| 6,231,815 | B1 | 5/2001 | Bainczyk et al. | |
| 6,245,782 | B1 | 6/2001 | Serebruany et al. | |
| 6,258,930 | B1 | 7/2001 | Gauch et al. | |
| 6,274,386 | B1 | 8/2001 | Harttig | |
| 6,281,008 | B1 * | 8/2001 | Komai et al. | 435/306.1 |
| 6,309,885 | B1 | 10/2001 | Probst et al. | |
| 6,329,179 | B1 * | 12/2001 | Kopreski | 435/91.2 |
| 6,409,528 | B1 | 6/2002 | Bodnar | |
| 6,579,672 | B1 | 6/2003 | Granger et al. | |
| 6,605,444 | B1 * | 8/2003 | Klein et al. | 435/7.9 |
| 6,720,417 | B1 | 4/2004 | Walter | |
| 6,776,959 | B1 * | 8/2004 | Helftenbein | 422/50 |
| 6,805,842 | B1 * | 10/2004 | Bodner et al. | 422/555 |
| 6,881,537 | B1 * | 4/2005 | Goudsmit et al. | 435/5 |
| 7,008,765 | B1 * | 3/2006 | Bussemakers et al. | 435/6 |
| 7,067,287 | B1 | 6/2006 | Sakurai et al. | |
| 7,282,371 | B2 * | 10/2007 | Helftenbein | 436/178 |
| 2002/0009722 | A1 | 1/2002 | Berger et al. | |
| 2002/0068821 | A1 | 6/2002 | Gundling | |
| 2002/0102570 | A1 | 8/2002 | Baker | |
| 2002/0150907 | A1 * | 10/2002 | Fomovskaia et al. | 435/6 |

FOREIGN PATENT DOCUMENTS

| | | |
|---|---|---|
| EP | 0554034 | 8/1993 |
| EP | 0389063 | 8/1997 |
| EP | 0 818 542 | 1/1998 |
| EP | 0818542 | 1/1998 |
| WO | 94/18156 | 8/1994 |
| WO | 97/05248 | 2/1997 |
| WO | WO97/05248 | 2/1997 |
| WO | 98/32877 | 7/1998 |

OTHER PUBLICATIONS

Chomczynski et al., Analytical Biochemisty 162 : 156-159 (1987).*
Curry et al., J. Clin. Oncol. 16 : 1760-1769 (1998).*
De Vires et al., Br J Cancer 80 : 883-8991 (1999).*
Farthmann et al., J. of Invest. Derm. 110:263-268 (1998).*
Foss et al., Br J Cancer 72 :155-159 (1995).*
Hoon et al., J. Clin Oncol 13 : 2109-2116 (1995).*
Keilholz et al., Euro J. Cancer 34 : 750-753 (1998).*
Keilholz et al., Melanoma Research 7 : S133-S141 (1997).*
Kunter et al., J Nat Cancer Inst. 88 : 590-594 (1996).*
Mellado et al., J. Clin Oncol 14 : 2091-2097 (1996).*
Smith et al., Lancet 338 : 1227-1229 (1991).*
Tobal et al. Invest Ophthamol. Vis Sci 34 : 2622-2625 (1993).*
Lozano, M.E., et al.(1993) "A Simple nucleic acid amplification assay for the rapid detection of Junin virus in whole blood samples", Virus Research, vol. 27, pp. 37-53, (XP002900733).
Mac Donald, R.J., et al. (1988) "Isolation of RNA using guanidinium salts", Chemical Abstracts, vol. 108, p. 324. (XP002900734).
Guide Mol. Cloning Tech. (1987), Methods Enzymd., vol. 152, pp. 219-227.
Andreas Pahl and Kay Brune, "Gene expression changes in blood after phlebotomy: implications for gene expression profiling"; Blood, Aug. 1, 2002—vol. 100, No. 3, pp. 1094-1095.
Andreas Pahl and Kay Brune, "Stabilization of Gene Expression Profiles in Blood after Phlebotomy"; Clinical Chemistry 48, No. 12, 2002, pp. 2251-2253.
Adeline R. Whitney, Maximilian Diehn, Stephen J. Popper, Ash A. Alizadeh, Jennifer C. Boldrick, David A. Relman and Patrick O. Brown, "Individuality and variation in gene expression patterns in human blood"; PNAS, vol. 100, No. 4, Feb. 18, 2003, pp. 1896-1901.
Mc Muller, K Merx, Z Weiber, X Kreil, T Lahaye, R Hehlmann and A Hochhaus, "Improvement of molecular monitoring of residual disease in leukemias by bedside RNA stabilization"; Leukemia (2002) 16, pages 2395-2399.
Lynne Rainen, Uwe Oelmueller, Stewart Jurgensen, Ralf Wyrich, Cynthia Ballas, Jim Schram, Chris Herdman, Danute Bankaitis-Davis, Nancy Nicholls, David Trollinger and Victor Tryon, "Stabilization of mRNA Expression in Whole Blood Samples"; Clinical Chemistry 48:11, pp. 1883-1890.
Raymond J. MacDonald, Galvin H. Swift, Alan E. Przybyla, and John M. Chirgwin, "Isolation of RNA Using Guanidinium Salts"; Methods in Enzymology, vol. 152 , (1987), pp. 219-227.
Christopher Hartel, Gregor Bein, Michael Muller-Steinhardt, and Harald Kluter "Ex vivo induction of cytokine mRNA expression in human blood samples"; Journal of Immunological Methods, 249, (2001) pp. 63-71.
Oelrichs, Robert B et al; The Explosive Human Immunodeficiency Virus Type 1 Epidemic among injecting Drug Users of Kathmandu, Nepal, is Caused by Subtype C Virus of Restricted Genetic ; Journal of Virology; vol. 74, No. 3, Feb. 2000, pp. 1149-1157.
Schmidt, Warren N., et al.; "Direct Detection of Hepatitis C Virus (HCV) RNA from Whole Blood and Comparison with HCV RNA in Plasma and Peripheral Blood Mononuclear Cells"; Journal of Virology; vol. 47, No. 2; 1995; pp. 153-160.
"BD Vacutainer plus EDTA Tubes," 2000, BD Vacutainer Systems, p. 1.
A Newsletter from Becton, Dickinson Vacutainer Systems, Lab Notes, vol. 8, No. 3, 1998, pp. 1-8.
Lahiri, D. K. et al; "DNA Isolation by a Rapid Method from Human Blood Samples; Effect of MGCL2, EDTA, Storage Time, and Temperature on DNA Yield and Quality," Biochemical Genetics, Plenum Press Co., London, GB, vol. 31, No. 7/8, Aug. 1993 (1993/08), pp. 321-323.
Holodniy, et al., J. Clin. Microbiology, 29:676-679 (1991).
Dawes, et al., Thrombosis Research, 12(5): 851-61 (1978).
Ludlam et al., Thrombosis Research, 6(6): 543-48 (1975).
Pfiefer, P.H. et al., "Possible mechanism for invitro complement activation in blood and plasma samples: futhan/EDTA controls in vitro complement activation," Clinical Chemistry, American Association for Clinical Chemistry. Winson, U.S., vol. 45, No. 8, Aug. 1999 (1999-08), pp. 1190-1199.
Kuhne, T. et al., "Flow Cytometric Evaluation of Platelet Activation in Blood Collected into EDTA vs. Diatube-H, A Sodium Citrate Solution Supplemented with Theophyline, Adenosine and Dipyridamole." American Journal of Hematology, New York, New York; US., vol. 50, No. 1, 1995, pp. 40-45.
Lozano, M.E. et al. (1993) "A simple nucleic acid amplification assay for the rapid detection of Junin virus in whole blood samples", *Virus Research*, vol. 27, pp. 37-53, (XP002900733).
Mac Donald, R.J. et al. (1988) "Isolation of RNA using guanidinium salts", *Chemical Abstracts*, vol. 108, p. 324. (XP002900734).

* cited by examiner 1 2 3 4

VESSEL FOR BLOOD SAMPLING

Matter enclosed in heavy brackets [ ] appears in the original patent but forms no part of this reissue specification; matter printed in italics indicates the additions made by reissue.

CROSS REFERENCE TO RELATED APPLICATIONS

Applicant claims priority under 35 U.S.C. §119 of GERMAN Application No. 198 36 559.4 filed on Aug. 12, 1998. Applicant also claims priority under 35 U.S.C. §120 of PCT/EP99/05857, filed on Aug. 12, 1999. The international application under PCT article 21(2) was not published in English.

The present invention relates to a vessel for withdrawing blood, and the blood withdrawn should especially be used for stabilizing and analyzing nucleic acids.

When blood is taken, it is normally collected in vessels which already contain anticoagulants such as heparin, citrate or EDTA. The blood is thereby prevented from coagulating. The blood samples obtained thereby can be stored at suitable temperatures for a long time. This way of obtaining blood has, however, considerable drawbacks when nucleic acids such as (m)RNA or DNA are to be analyzed. For such purposes the nucleic acids contained in the sample should optimally be stabilized already at the moment of withdrawal, i.e. a degradation of the existing nucleic acids should be prevented, but also the new synthesis of mRNA.

This objective of a stable storage of the nucleic acids contained in the sample material, i.e. from the moment of withdrawal, has not been achieved yet in practice for the following reasons:

Cells contain nucleases, enzymes, which destroy nucleic acids as soon as they come into contact with the substrates thereof (RNA, DNA). The effect of cellular and extracellular nucleases is normally under physiological control as long as the cells are in their normal environment. The withdrawal of blood effects more or less strong changes in the nucleic acids contained in the cells. Nucleases are then released within the cells and/or by the lysis of cells to the outside. Moreover, nucleic acids are synthetized more or less strongly. In particular the long-term storage of blood leads to aging and destruction of the cells.

Another problem arising in the long-term storage of blood samples obtained according to standard withdrawal methods is the considerable change in the sample material. Such changes, e.g. strong lysis of cells, may have the effect that the standard methods for isolating nucleic acids no longer function in an adequately efficient way.

Apart from the problems regarding a stable storage of nucleic acids contained in the sample material, further difficulties arise in the conventional method for withdrawing blood. The conventional anticoagulants are often not separated efficiently enough during isolation of nucleic acids and interfere with in the subsequent analysis of nucleic acids, e.g. in the case of amplification by means of PCR (polymerase chain reaction). Heparin is e.g. a generally known inhibitor of PCR.

Finally, the question arises in the quantitative analysis of nucleic acids how the whole method ranging from sampling to the measurement of nucleic acids can be controlled under standardized conditions. Ideally, a quantitatively and qualitatively defined standard nucleic acid should already be added to the sample material during withdrawal and should be subjected to the whole process of sampling and determination. This can also not be accomplished with the conventional withdrawal systems.

A further drawback of conventional blood withdrawal is the risk of transferring infectious material because manual process steps have so far been needed for the isolation of nucleic acids. Contact with potentially infectious germs cannot be ruled out.

In the literature there is described a method in which the blood sample is mixed with guanidinium salt directly after withdrawal from a patient (EP 0 818 542 A1). In this method the guanidinium salt is present in powder form to thereby exploit the increased stability of the guanidinium salt. This method, however, has serious drawbacks because the salt, for instance, must first dissolve in the added blood. This dissolution process depends, in particular, on the temperature and cannot be controlled because of the nontransparent sample material used. The use of a corresponding product for diagnostic medical purposes is thus very problematic.

Furthermore, nucleases are extremely active enzymes which can only be inhibited under extremely denaturing conditions. Denaturation depends on the concentration of the guanidinium salt in solution. An inhibiting concentration of guanidinium salt in solution does not exist in the cited method right from the beginning. Thus, there is an uncontrolled degradation of nucleic acids during the dissolution process. Moreover, in this method the addition of reducing agents is omitted, without which an efficient inhibition, in particular of RNases, is not ensured (see Example no. 5).

Moreover, the sample prepared in this way cannot directly be used for the further nucleic acid isolation on glass surfaces. Moreover, the use of guanidinium salt powder does not permit the addition of internal nucleic acid standards. Such standards are mandatory for process control and exact quantification.

The present invention has been based on the technical problem of providing a vessel for withdrawing blood which does not have the drawbacks of the prior art. In particular, it should be possible to subject the sample taken with the vessel directly to the standard methods for analyzing nucleic acids without the need for further sample preparation steps.

According to the invention this problem is solved by a vessel for withdrawing blood, the vessel containing an aqueous solution comprising the following components:

a guanidinium salt;
a buffer substance;
a reducing agent; and/or
a detergent.

The vessel of the invention has the following advantages: 1. Blood is already lysed at the moment of withdrawal in that the withdrawal vessel already contains a nucleic acid-stabilizing substance in solution. 2. The nucleic acid-stabilizing substance is composed such that the sample material, in particular the nucleic acids contained therein, are directly stabilized upon contact with the solution. 3. In contrast to all of the former standard withdrawal systems, such as EDTA or heparin-containing withdrawal vessels, the stabilized sample need no longer be handled as infectious material. 4. The nucleic acid-stabilizing substance is composed such that the sample material can directly be used in subsequent isolating methods. 5. The nucleic acid-stabilizing substance can be separated during subsequent isolation so efficiently that an inhibition of PCR is not observed. 6. The nucleic acid-stabilizing substance may have added thereto an internal standard. This permits the control of the whole method from the moment of sampling up to the detection of nucleic acids.

The withdrawal vessel mentioned under item 1 is a conventional blood withdrawing vessel (small tube) which has introduced thereinto a defined volume of a nucleic acid-stabilizing substance. The small tube is then preferably subjected to a defined vacuum which guarantees that only a specific volume of blood can flow thereinto during withdrawal. The small tube can be handled by conventional blood-taking methods. The solution contained in the tube contains the following reagents in a specially preferred embodiment: Guanidinium thiocyanate, Triton-X-100, dithiothreitol and a suitable buffer system, such as citrate, Tris or HEPES. In the described composition the solution is compatible with the vacuum tube. This solution can be stored in the vacuum tube without any problems and without any impairment of the desired stabilizing function. The whole system presents no problems, in particular to blood donors, and is safe during sampling.

The solution containing the guanidinium salt, the buffer substance, the reducing agent and/or the detergent is stable in storage and converts the supplied and freshly taken blood into a material which is also stable in storage and can directly be subjected to the standard nucleic-acid analysis kits (e.g. those of Roche or Qiagen).

Guanidinium thiocyanate and/or guanidinium chloride are preferred as guanidinium salt.

Preferably, the guanidinium salt is present in a concentration of 2.0 to 8.0 M. Tris or citrate is preferred as the buffer substance, the exact pH being preferably adjusted with HCl. Further possible buffers are however HEPES, MOPS, citrate and phosphate buffer, such as PBS.

The buffer concentration is preferably between 10 and 300 mM, particularly preferably between 10 and 100 mM.

Triton-X-100 is preferred as the detergent. Further possible detergents are NP40, Tween 20, polydocanol or other detergents.

The detergent concentration is preferably at 5 to 30% (w/v), particularly preferably at 10 to 20% (w/v).

DTT is preferred as the reducing agent, but β-mercaptoethanol, TCEP (Tris(2-carboxyethyl)phosphine) or other reducing agents can also be used.

The preferred concentration of the reducing agent is at 0.1 to 10% (w/v), particularly preferred are 0.5 to 2% (w/v).

The pH of the solution is preferably at 3.0 to 9.0, particularly preferably at 4.0 to 7.5, particularly preferably at 5 to 6.

The pH of the solution is in particular chosen such that a pH ranging from 5.0 to 7.6 is set after addition of the sample material. Particularly preferred is a pH between 6.3 and 6.9 (see Example no. 8).

A particularly preferred solution preferably contains 4 M guanidinium thiocyanate, 45 mM Tris/HCl, 18%, preferably 15% (w/v) Triton-X-100, 0.8% (w/v) DTT and has a pH of 6.0.

In a further preferred embodiment the volume for receiving the blood sample has a negative pressure which can be adjusted such that a previously determined blood volume is sucked into the vessel after a blood vessel has been pierced. Correspondingly evacuated vessels are available on the market.

The vessel which contains the blood taken can then immediately be subjected to further analyses or, however, may be stored for a long period of time (up to several days) without any disadvantages for the quality of the sample.

In the method of the invention the freshly taken blood is directly contacted in the blood withdrawing vessel with the above-described solution so that all processes which might change the nucleic acid pattern of the sample are immediately stopped. Therefore, the data determined at a later time with respect to the detected nucleic acids very accurately represent the actual state at the time of blood withdrawal, i.e. both with respect to the quantities and the types of nucleic acids.

Preferably, the blood amount taken is 0.1 to 4 times the solution fed into the vessel. The solution is preferably 0.5 to 5.0 ml. Thus the final concentration of guanidinium salt after blood addition is at 1.0 to 5 M, preferably at 1 to 3 M, particularly preferred are 2-3 M (see Example 7).

The vessel according to the invention is preferably used for blood withdrawal when the blood sample is to be used for analyzing nucleic acids. The use of the above-mentioned solution as a component of the described withdrawal system solely guarantees the immediate lysis of the cells and the simultaneous stabilization of the sample by immediate inactivation of the nucleases. Surprisingly, the blood sample obtained thereby can be stored even at room temperature or higher for several days. Moreover, the withdrawal system guarantees a contamination-free and non-infectious handling ranging from sampling via nucleic acid isolation to analysis. In the conventional methods of nucleic acid isolation, additional handling steps have so far been required (e.g. the transfer of the blood sample taken into the reagents for nucleic acid isolation, etc.), which entails an additional risk of infection.

The sample obtained with the blood withdrawing system is compatible with all of the conventional standard methods of nucleic acid isolation. Particular attention should here be paid to methods which are based on the binding of nucleic acids to glass surfaces, but also sequence-specific binding to complementary nucleic acid and solvent-based extraction methods.

Thus the invention as described consists of a blood withdrawing system which is conceived such that the following conditions are satisfied. 1. Controlled sampling and simultaneous stabilization of the nucleic acids (DNA, RNA) contained in the sample material. 2. Sampling in which the use of anticoagulants can be completely omitted. 3. The sample obtained by way of the above-described blood withdrawing system can be used in a universal manner in all of the known systems for isolating nucleic acids. 4. The blood withdrawing system is stable in storage.

Additionally, it has surprisingly been found that the sample obtained by way of the described withdrawal system can be stored in the vessel for a long period of time without degradation of the nucleic acids (see Examples 2, 3, 7, 8).

The following examples will explain the invention:

EXAMPLE 1

The blood withdrawing system may be composed in a preferred embodiment as follows (see FIG. 1): A small tube is filled with a defined volume of the nucleic acid-stabilizing substance and is provided with a defined vacuum and sealed with a septum. The septum is constructed such that it is compatible with the standard sampling accessories (cannula, etc.). In the present example 2.2 ml reagent was supplied and the vacuum was adjusted such that exactly 2.2 ml blood could flow in during sampling. The nucleic acids contained in the inflowing blood flow were immediately converted into a stable form.

General preliminary remark regarding the following examples.

In all of the examples described hereinbelow, the nucleic acid-stabilizing substance (N-sS) had, unless indicated otherwise, the following composition: 45 mM Tris, 5 M guanidinium thiocyanate (GTC), 0.8% (w/v) dithiothreitol (DTT), 18% (w/v) Triton-X-100, pH 6.0.

In all of the examples described, the nucleic acid-stabilizing substance was, unless indicated otherwise, mixed with the sample in the ratio of 1 to 1 (1 volume N-sS plus 1 volume sample material). A lower concentration of N-sS, e.g. 1 volume N-sS plus 5 volumes sample, might effect a degradation of RNA.

Blood was stabilized for all examples by directly feeding the blood upon withdrawal into the small tube mixed with N-sS.

EXAMPLE 2

Stability of nucleic acid after mixture of sample material and N-sS. Isolation of RNA and DNA from the sample lysate with silica-derivatized surfaces.

Material and Method

The sample material for the DNA and RNA isolation was directly used after withdrawal, after storage at 4° C. for 6 days, and after storage at −20° C. for 1 month.

Figure 2:
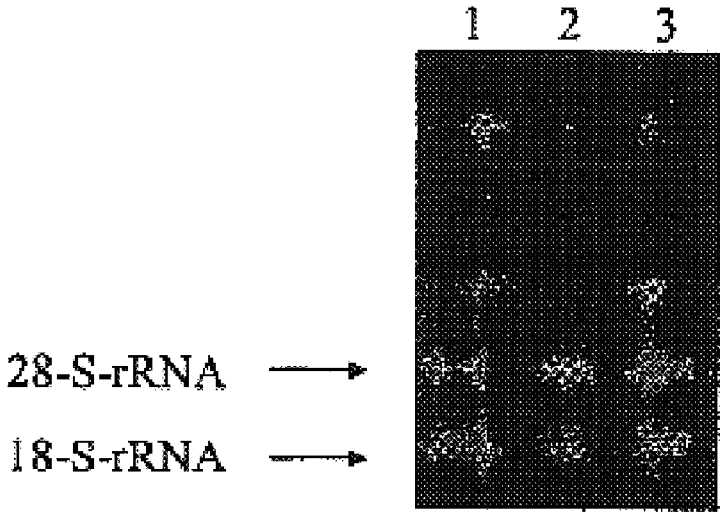

The High Pure RNA Isolation Kit (Boehringer Mannheim, cat. no. 1828 665) was used for isolating RNA (FIG. 2). The instructions given in the package leaflet were modified as follows: A volume of 2.4 ml sample lysate was applied in 4 aliquots at 600 μl each to the column, so that a sample material of 2.4 ml lysate was applied on the whole. All of the other steps were carried out in accordance with the package leaflet. The RNA was finally eluted with 100 μl elution buffer.

Figure 3:
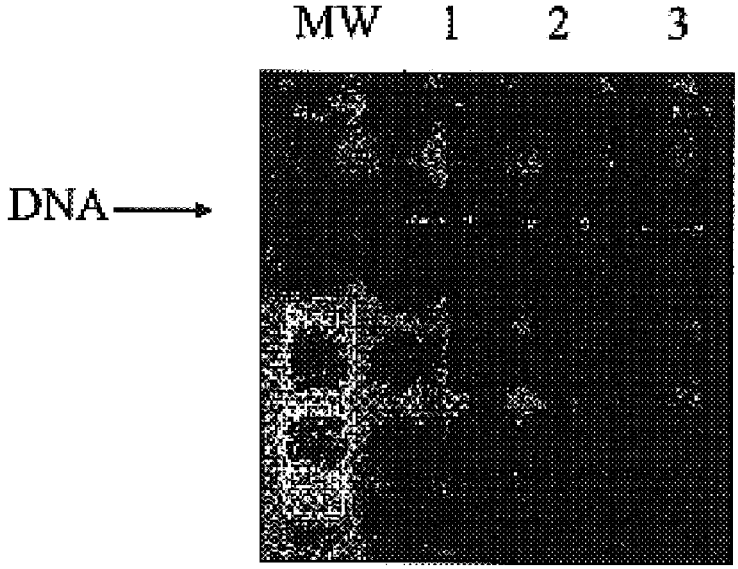

For the isolation of DNA (FIG. 3) the QiaAmp Blood Kit (Qiagen cat. no. 29104) was used. The standard procedure described in the package leaflet was modified in various points: 400 μl sample volume was directly applied to the column; the binding reagent contained in the kit was not used. 25 μl proteinase-K batch solution was added and the sample was incubated at room temperature for 10 min. Subsequently, the column was put into a collection vessel and centrifuged as described in the package leaflet. All of the further steps were carried out in accordance with the description in the package leaflet, except for the use of ethanol. The elution volume was 200 μl.

EXAMPLE 3

Figure 4:
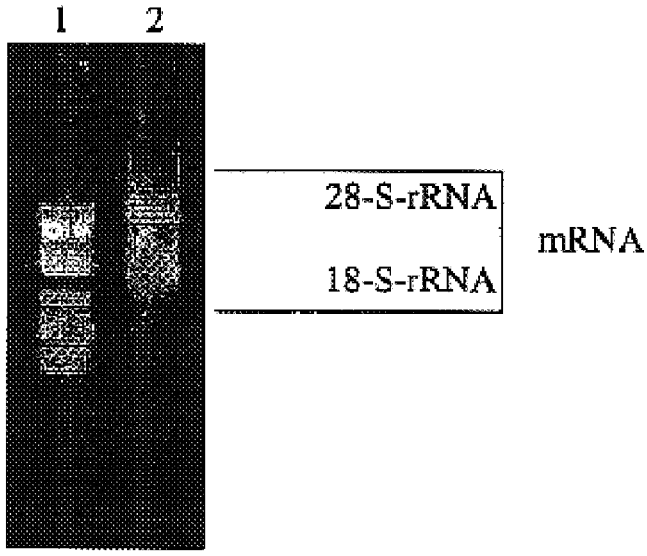

Isolation of mRNA from sample lysate using streptavidin-coated magnetic particles and biotin-labeled Oligo(dT) (FIG. 4):

Material and Method 20 ml sample lysate was fed into a vessel. The mRNA was isolated according to the following method: First of all 30 ml hybridization buffer (20 mM Tris-HCl, 300 mM NaCl, 6 nM biotin-labeled Oligo(dT), pH 7.4) was added to the lysate. 3 mg streptavidin magnetic particles (Boehringer Mannheim) were then added. The sample was mixed and incubated at room temperature for 5 min. The magnetic particles were separated with the help of a magnet; the supernatant was discarded. The particles were then resuspended in wash buffer 1 (10 mM Tris-HCl, 200 mM NaCl, 1% Triton-X-100, pH 7.5) and washed three times with wash buffer 2 (10 mM Tris-HCl, 200 mM NaCl, pH 7.5) (wash steps: resuspension, magnetic separation, removal of the supernatant). After the last wash step the supernatant was completely removed and the particles were resuspended in 20 μl distilled water. The sample was heated to 70° C. for 5 min. The magnetic particles were separated, and the supernatant which contained the mRNA was analyzed by means of gel electrophoresis.

EXAMPLE 4

Figure 5:
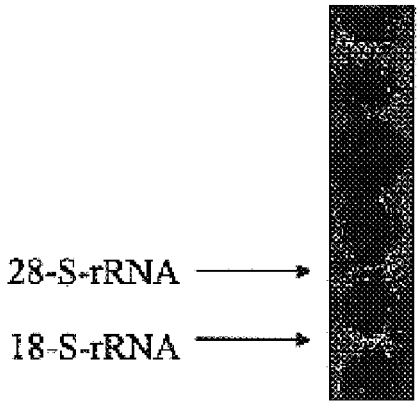

Isolation of DNA and RNA using a modified rule according to Chomczynski and Sacchi (Analytical Biochemistry 162, 156-159 (1987)) (example of a method based on solvent extraction) (FIG. 5):

Material and Method 2 ml sample volume was transferred from the blood withdrawing vessel into a small tube. 0.2 ml of a 2 M sodium acetate solution, pH 4, 2 ml phenol (water saturated) and 0.4 ml of a chloroform-isoamyl alcohol mixture (49:1) were then added, the sample being thoroughly mixed after addition of each solution. The complete solution was vigorously shaken for 10 seconds and incubated on ice for 15 minutes. The sample was centrifuged for 20 minutes at 4° C. at 10000 g. After centrifugation the RNA was in the aqueous phase; the DNA and proteins in the intermediate and phenol phase. The aqueous phase was transferred into a new vessel and mixed with 1 ml isopropanol. For precipitating the RNA the sample was stored at −20 C. for 1 hour. After renewed centrifugation at 4° C. at 10000 g the RNA was pelleted. The pellet was resuspended in 0.3 ml buffer (4 M guanidinium thiocyanate, 25 mM sodium citrate, pH 7.0, 0.5% sarcosyl, 0.1 M 2-mercaptoisopropanol), transferred into a new 1.5 ml Eppendorf vessel and mixed with 1 volume of isopropanol. After incubation at −20° C. for 1 hour the solution was centrifuged in an Eppendorf centrifuge at 4° C. for 10 minutes. The RNA pellet was received in 75% ethanol and concentrated by centrifugation (Speed vac) and dried. For further processing the sample was dissolved in 100 μl 10 mM Tris-HCl, pH 6.5.

EXAMPLE 5

Importance of reducing reagents (such as DTT) in the stabilizing solution for the longterm stability of RNA Material and Method Stabilizing solution used: 4.0 M GTC; 13.5% Triton X100; 45 mM Tris//HCl; with or without 120 mM DTT. 700 μl serum was mixed with 700 μl stabilizing solution. After incubation for 2 min 20 μl MS2-RNA (0.8 μg/μl of Roche) was added. The samples were incubated at 40° C. for 180 min and then processed in aliquots of 400 μl each with the High Pure total RNA Kit of Roche. The samples were applied in one step to the column without addition of the binding reagent of the kit and centrifuged in accordance with the instructions. The following wash steps and the elution of the RNA in 50 μl elution buffer were carried out in accordance with the instructions.

Figure 6:
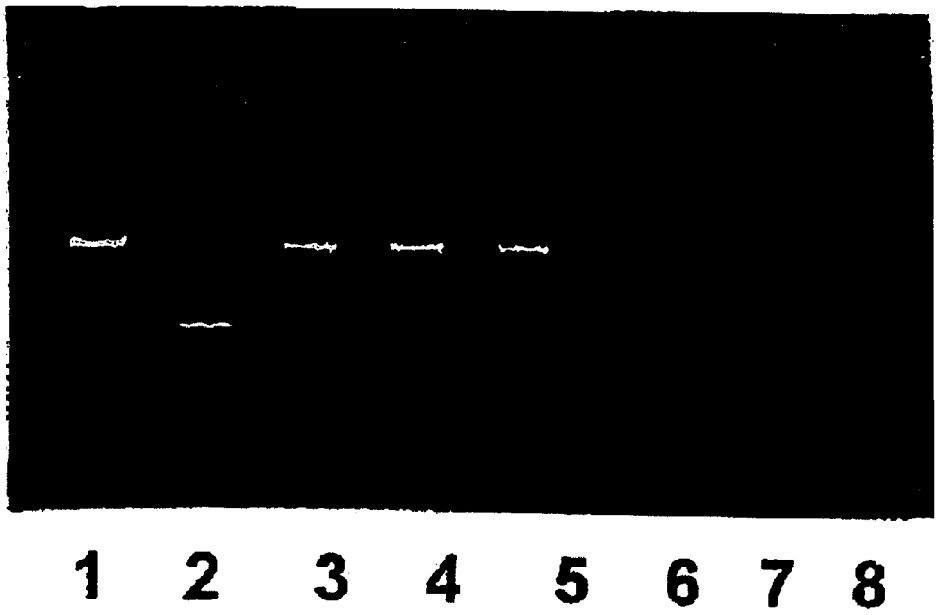

The analysis was carried out by means of agarose gel (see FIG. 6). Result: Without the addition of reducing reagents to the stabilizing solution no long-term stabilization of RNA can be achieved.

EXAMPLE 6

Stability of Free MS2-RNA in Serum. Kinetics of the RNA Degradation by Sample Components Material and Method 250 μl serum was spiked with 10 μl MS2-RNA (0.8 μg/μl of Roche) and incubated at room temperature. Immediately after the addition of RNA, after 2 min to 50 min, the natural RNA degradation in serum was stopped by adding 250 μl stabilizing solution. All batches were analyzed twice. As a standard, a sample was only mixed with MS2-RNA after addition of the stabilizing solution to the serum and was processed in parallel.

Figure 7:
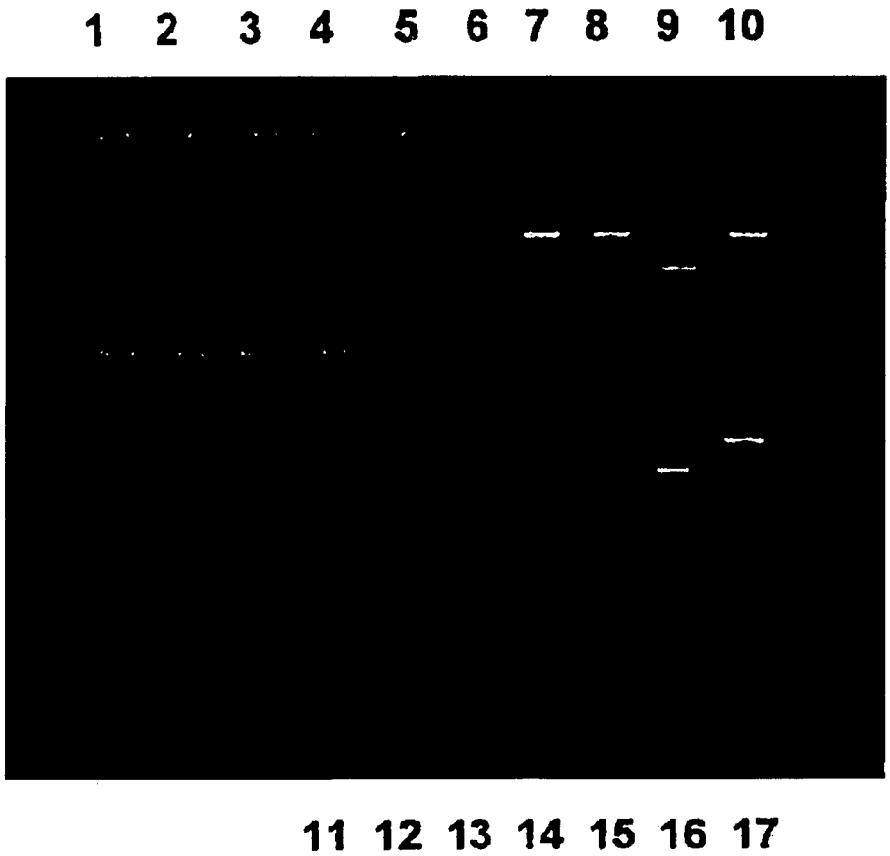

All samples were processed in parallel with the High Pure viral RNA Kit of Roche. The samples were applied to the column in one step without addition of the binding reagent of the kit and centrifuged according to instructions. The following wash steps and the elution of RNA in 50 μl elution buffer were carried out according to instructions. 20 μl of the eluate was separated by means of a 1.2% native agarose gel and analyzed (see FIG. 7).

Result: MS2-RNA is not stable in serum. Already 2 minutes after addition of RNA to the serum the RNA is completely degraded. By the addition of stabilizing solution to the serum in the ratio of 1:1, this process can be stopped immediately, and a stabilization of the RNA can be achieved at the time when the stabilizing solution is added (=blood withdrawal).

EXAMPLE 7

Stability of MS2-RNA in Serum/stabilization Solution. Dependence on the GTC Concentration Material and Method Stabilization solutions used: 3-5 M GTC; 13.5% Triton X100; 50 mM DTT; 42 mM Tris/HCl pH of the solutions: about 4.0 pH of the solutions after addition of serum: about 6.7.

2 ml serum was mixed with 2.5 ml of the respective stabilization solutions. After an incubation time of 2 to 5 min 90 μl MS2-RNA (0.8 μg/μl of Roche) was added and incubated at 40° C. 400 μl samples were taken at regular intervals and processed with the High Pure total RNA Kit of Roche according to Example 5. The samples were eluted in 50 μl and frozen at −20° C. For the analysis of the RNA integrity 20 μl of the eluate was applied to a 1.5% agarose gel (see FIG. 8).

For the PCR analysis of the samples 10 μl of the eluate was reversely transcribed by means of AMV-RT (Roche) and subsequently analyzed by means of PCR on the Lightcycler:

| | |
|---|---|
| Batch for RT: | 4.0 μl AMV-RT buffer |
| (42° C. for 1 h) | 2.0 μl dNTP's (final concentration 10 mM) |
| | 0.5 μl RNase inhibitor (Roche, 20 units) |
| | 1.0 μl Primer 2827 (final concentration 1 μM) |
| | 1.9 μl DMPC water |
| | 0.6 μl AMV-RT (Roche, 15 units) |
| | 10 μl template RNA |
| Σ | 20 μl |

The PCR was carried out on the Lightcycler at an annealing temperature of 61° C. using SYBR-Green as detection system. Batch for PCR:

| | |
|---|---|
| | 1.6 μl $MgCl_2$ (batch solution 25 mM) |
| | 5.9 μl DMPC water |
| | 0.25 μl Primer 2827 (batch solution 20 mM) |
| | 0.25 μl Primer 2335 (batch solution 20 mM) |
| | 1.0 μl SYBR-Green-Mastermix (Roche) |
| | 1.0 μl RT batch (1:50 diluted) |
| Σ | 10 μl |

Figure 9:
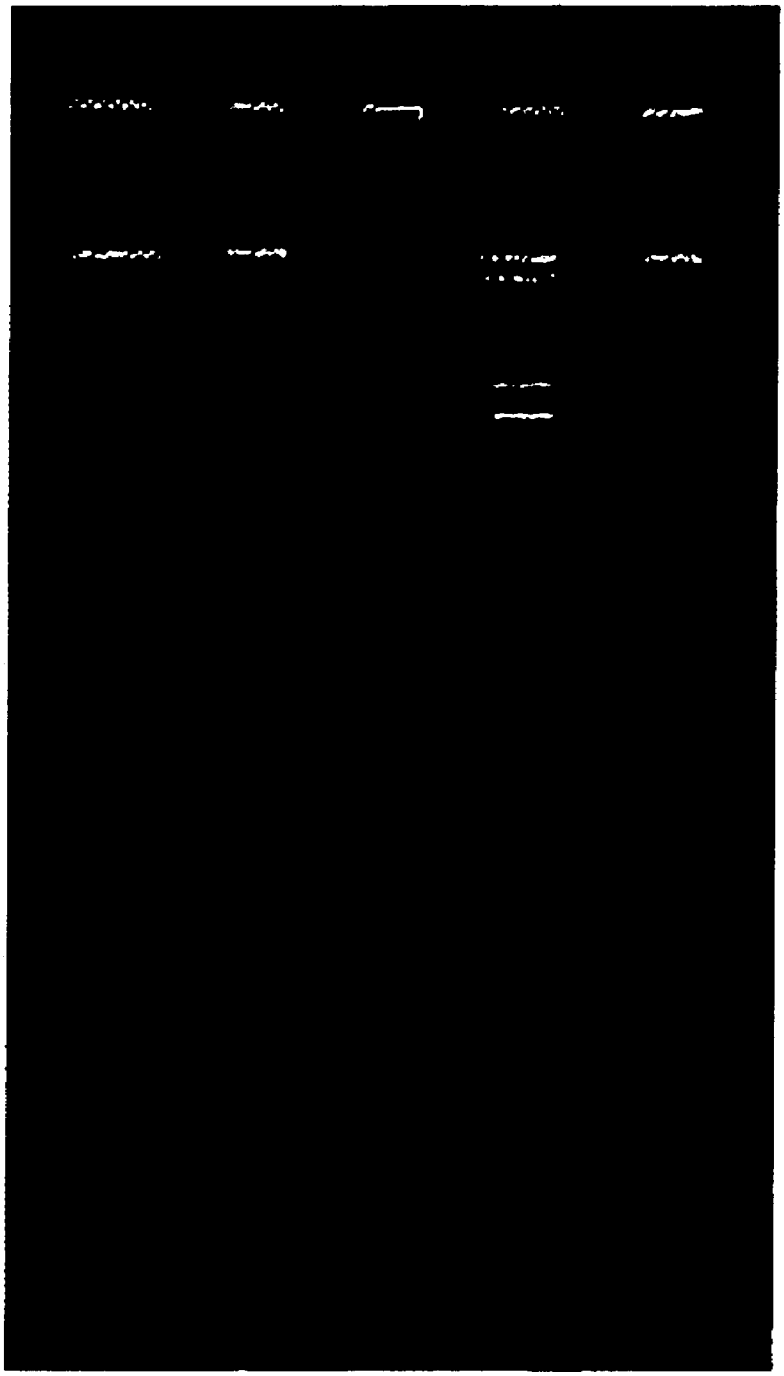

The amplificate of the PCR was completely applied to a 2% agarose gel (see FIG. 9).

Result:

RNA integrity at 40° C. after 3 days.

Figure 8:
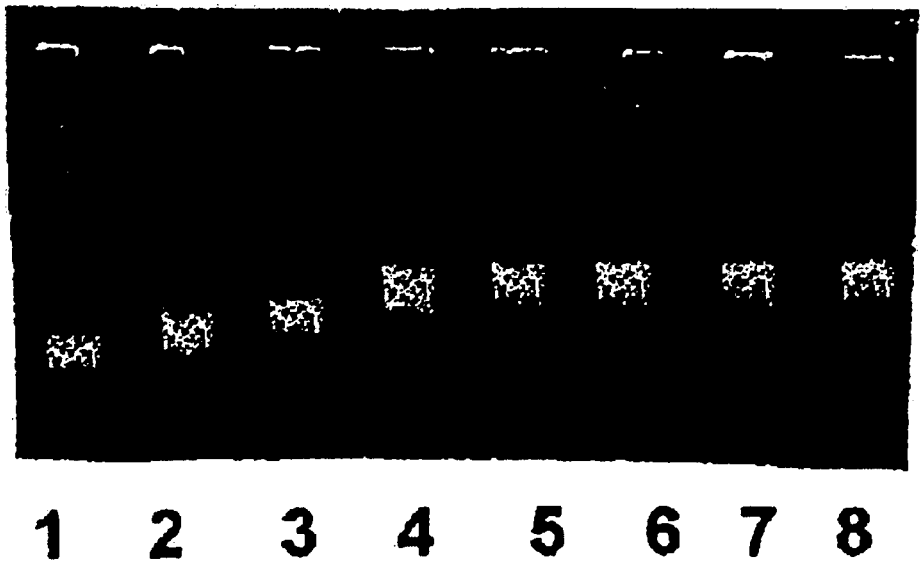

The agarose gel in FIG. 8 shows 20 μl of the eluted MS2-RNA after incubation at 40° C. for 3 days. After this period distinct differences in the RNA integrity can be made out in dependence upon the GTC content. Thus a salt content of less than 2 M in the serum/stabilization solution is of advantage to the integrity of the RNA.

Amplificability of the RNA at 40° C. after 8 days.

Although a beginning degradation of the RNA was already detected at 40° C. after 3 days, all of the RNA samples could be amplified after an incubation of 8 days at 40° C. and clearly detected.

The amplificate of the PCR was fully applied to a 2% agarose gel (see FIG. 9).

EXAMPLE 8

Stability of MS2-RNA in Serum/stabilization Solution: Dependence on the pH of the Sample Mixed with Stabilization Solution Material and Method

| | | |
|---|---|---|
| Solution used: | 4M (5M) | GTC |
| | 14.4% | Triton X 100 |
| | 50 mM | DTT |
| | 45 mM | Tris/HCl |

pH after serum addition between 6.7 and 8.0

Figure 10:
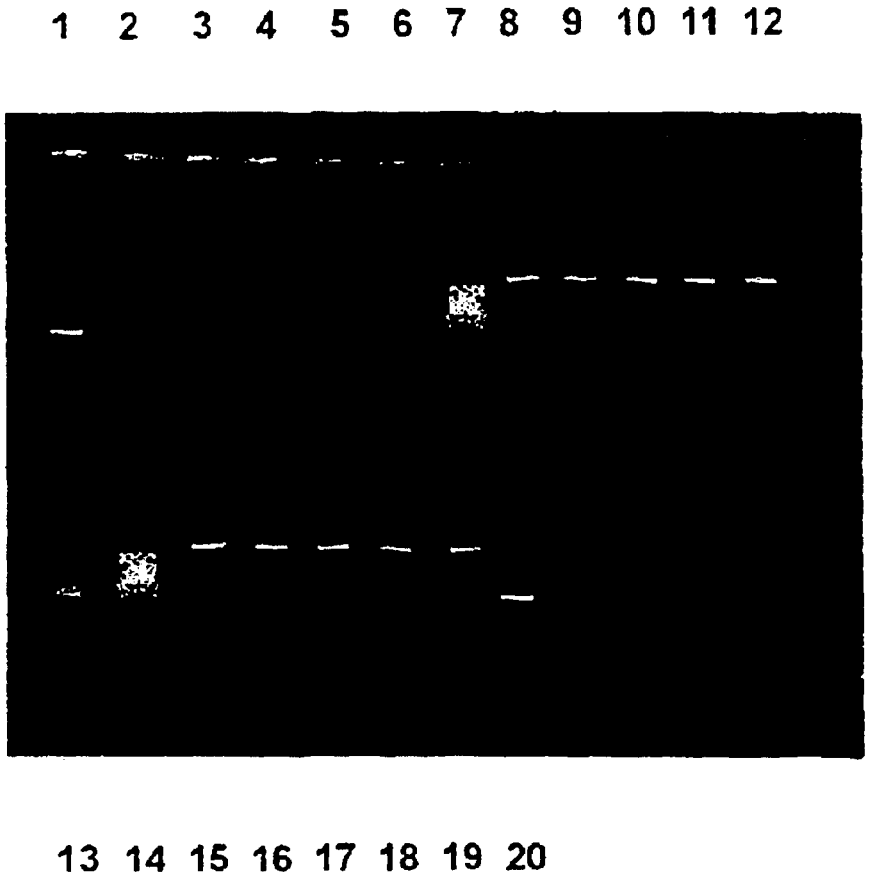

2.5 ml stabilization solution was mixed with 2.0 ml serum. After addition of 90 μl MS2-RNA (0.8 μg/μl, Roche) the samples were incubated at room temperature. The RNA was processed at regular intervals from 500 μl sample with the Roche viral RNA kit according to Example 6 and isolated in 50 μl elution buffer. 20 μl of the eluate was analyzed by means of agarose gel (see FIG. 10).

Result:

The pH of the serum/stabilization solution and thus the pH and the buffer range of the stabilization solution are decisive for the long-term stabilization of RNA. While at a pH of 8.0 an intact RNA could no longer be detected already after 2 days, intact RNA is still detectable within a pH range between 6.6 and 7.0 after 13 days of incubation at room temperature.

Apart from the pH, however, an optimally adjusted GTC concentration is also of importance to the long-term stabilization of RNA (see also Example 7). The illustrated example demonstrates that a GTC final concentration in the stabilized sample of 2.2 M GTC is better than 2.78 for a long-term stabilization of RNA.

Legends

FIG. 1:

Sampling vessel with N-sS, defined vacuum, sealed with septum.

FIG. 2:

Gel analysis (1% agarose) of RNA which was stored in the sampling vessel for different periods of time. Column 1: Isolation directly after sampling (no storage), column 2: storage for one month at −20° C., column 3: storage for 6 days at 4° C. The amount of the applied RNA corresponded to a blood volume of 120 μl.

FIG. 3:

Gel analysis (1% agarose) of DNA which was stored in the sampling vessel for different periods of time. Column 1: isolation directly after sampling (no storage), column 2: storage for one month at −20° C., column 3: storage for 6 days at 4° C. The amount of the applied DNA corresponded to a blood volume of 10 μl.

FIG. 4:

Gel analysis (1% agarose) of mRNA which was isolated from 10 ml blood (column 2). Molecular weight marker (column 1). In addition to the mRNA, the rRNA bands are visible. The sharp contours of the bands demonstrate the integrity of the nucleic acids.

FIG. 5:

Gel analysis (1% agarose) of the RNA which was isolated from 120 μl blood.

FIG. 6:

Gel analysis of isolated MS2-RNA after incubation in serum/stabilization solution with/without DTT for 180 min at 40° C.

Column 1: positive control: MS2-RNA, column 2: DNA marker, column 3,4,5: MS2-RNA after incubation with DTT-containing stabilization solution, column 6,7,8: MS2-RNA after incubation with stabilization solution without DTT.

FIG. 7:

Gel analysis of isolated MS2-RNA after incubation in serum for 0-50 min

Column 10,17: MS2-RNA standard, column 9,16: DNA marker, column 7,8: incubation for 0 min, column 5,6: incubation for 2 min, column 3,4: incubation for 5 min, column 1,2: incubation for 10 min, column 11,12: incubation for 15 min, column 13,14: incubation for 30 min, column 15: incubation for 50 min

FIG. 8:

Gel analysis of MS2-RNA which was isolated after incubation in serum/stabilization solution for 3 days at 40° C. The GTC content of the stabilization solution after serum addition in which the relevant RNA sample was incubated is indicated in the corresponding column. Column 1: 2.70 M GTC, column 2: 2.5 M GTC, column 3: 2.36 M GTC, column 4: 2.20 M GTC, column 5: 2.08 M GTC, column 6: 1.94 M GTC, column 7: 1.80 M GTC, column 8: 1.66 M GTC.

FIG. 9:

Gel analysis of the PCR amplificates of MS2-RNA which was isolated after 1 day and 8 days, respectively, of incubation at 40° C. in serum/stabilization solution.

Column 1: Amplificate of the RNA isolated after 1 day, column 2: amplificate of the RNA isolated after 8 days, column 3: DNA marker, column 4: MS2-RNA positive control: 0.8 μg in 10 μl RT, 1:50 diluted, 1 μl amplified.

FIG. 10:

Gel analysis of isolated MS2-RNA after 6 days (column 2-12) and 13 days (column 14-19), respectively, of incubation at room temperature in serum/stabilization solution. The pH which was obtained after mixing of serum and stabilization solution is written behind the corresponding columns.

Column 1, 13, 20: DNA marker, column 2: pH 8.0, column 3: pH 7.7, column 4: pH 7.5, column 5: pH 7.35, column 6: pH 7.18, column 7,14: pH 7.07, column 8,15: pH 6.94, column 9,16: pH 6.8, column 10,17: pH 6.72, column 11,18: pH 6.68 and column 12,19: pH 6.7. The stabilization solution of RNA in column 12, 19 had the same pH as that of the RNA in column 11, but contained 5 m GTC instead of 4 M.

What is claimed is:

1. A blood withdrawing vessel *comprising:*

*an evacuated chamber which is provided for receiving withdrawn blood* containing a nucleic acid-stabilizing aqueous solution for stabilizing nucleic acids in [the] withdrawn blood directly upon contact with the solution,

*wherein* the solution [comprising] *comprises* the following components:

a guanidinium salt in a concentration of 1 to 8.0 M;

a buffer substance in a concentration of 10 to 300 mM;

a reducing agent in a concentration of 0.1 to 10%, by wt; and a detergent in a concentration of 5 to 30%, by wt.

2. The vessel according to claim 1, characterized in that the guanidinium salt is selected from guanidinium thiocyanate and guanidinium chloride.

3. The vessel according to claim 1, characterized in that the guanidinium salt is present in a concentration of 2.5 to 8.0 M.

4. The vessel according to claim 1, characterized in that the buffer substance is selected from Tris, HEPES, MOPS, citrate and phosphate buffer.

5. The vessel according to claim 1, characterized in that the detergent is selected from Triton-X-100, NP-40, polydocanol and Tween 20.

6. The vessel according to claim 1, characterized in that the reducing agent is selected from dithiothreitol, β-mercaptoethanol and TCEP.

7. The vessel according to claim 1, characterized in that the pH of the solution is between 4.0 and 7.5.

8. The vessel according to claim 1, characterized in that the solution contains the following components:

4 m guanidinium thiocyanate;

45 mM Tris/HCl;

15% (w/v) Triton-X-100;

0.8% (w/v) DTT;

wherein the [PH] *pH* is at 6.0.

[9. The vessel according to claim 1, characterized in that it has a vacuum in the chamber which is provided for receiving blood.]

10. The vessel according to claim 1, characterized in that it contains withdrawn blood.

11. A method of withdrawing blood, comprising the step of directly introducing the blood into a vessel according to claim 1.

12. The method according to claim 11, characterized in that an amount of blood is withdrawn that is 0.1 to 4 times the volume of the solution in the vessel.

13. The method according to claim 12, characterized in that the concentration of the guanidinium salt after the blood is introduced is between 1.0 M and 5 M.

14. A method for stabilizing and/or isolating nucleic acids from blood, comprising the step of introducing blood into a vessel according to claim 1 and, optionally, isolating the nucleic acids with conventional methods.

15. The method according to claim 11, characterized in that the pH of *the resultant mixture of* the solution [is adjusted such that, following the introduction of the blood, a pH between 4.0 and 7.5 is obtained] *and blood is between 5.0 and 7.6*.

16. The vessel according to claim 7, characterized in that the pH of the solution is between [4.0 and 6.5] *5.0 and 6.0*.

17. The method according to claim 13, characterized in that the concentration of the guanidinium salt, after blood is introduced, is between 1.5 and 5 M.

18. A blood withdrawing vessel *comprising:*

*an evacuated chamber which is provided for receiving blood* containing a nucleic acid-stabilizing aqueous solution for stabilizing nucleic acids in [the] blood directly upon contact with the solution,

*wherein* the solution [comprising] *comprises* the following components:

a guanidinium salt in a concentration of 1 to 8.0 M;

a buffer substance in a concentration of 10 to 300 mM;

a reducing agent in a concentration of 0.1 to 10%, by wt.

19. The vessel according to claim 18, characterized in that the guanidinium salt is selected from guanidinium thiocyanate and guanidinium chloride.

20. The vessel according to claim 19, characterized in that the guanidinium salt is present at a concentration of 2.5 to 8.0 M.

21. The vessel according to claim 18, characterized in that the buffer substance is selected from Tris, HEPES, MOPS, citrate and phosphate buffer.

22. The vessel according to claim 18, characterized in that the reducing agent is selected from dithiothreitol, β-mercaptoethanol and TCEP.

23. The vessel according to claim 18, characterized in that the pH of the solution is between 4.0 and 7.5.

24. The vessel according to claim 23, characterized in that the pH of the solution is between [4.0] *5.0* and 6.5.

[25. The vessel according to claim 18, characterized in that it has a vacuum in the chamber which is provided for receiving blood.]

26. The vessel according to claim 18, characterized in that it contains withdrawn blood.

27. A method of withdrawing blood, comprising the step of directly introducing the blood into a vessel according to claim 18.

28. The method according to claim 27, characterized in that an amount of blood is withdrawn that is 0.1 to 4 times the volume of the solution in the vessel.

29. The method according to claim 28, characterized in that the final concentration of the guanidinium salt after blood supply is between 1.0 M and 5 M.

30. The method according to claim 29, characterized in that the final concentration of the guanidinium salt after blood supply is between 1.5 M and 5 M.

31. The method according to claim 29, characterized in that the pH of *the resultant mixture of* the solution [is adjusted such that, following the addition of the sample material, a pH between 4.0 and 7.5 is obtained] *and blood is between 5.0 and 7.6*.

32. A method for stabilizing and/or isolating nucleic acids from blood, comprising the step of introducing blood into a vessel according to claim 18 and, optionally, isolating the nucleic acids with conventional methods.

33. A stabilized blood sample obtainable by introducing whole blood into a vessel according to claim 18.

34. The blood sample according to claim 33, characterized in that it has a pH of [4.0 to 7.5] *5.0 to 7.6*.

35. The blood sample according to claim 34, characterized in that it has a pH of [6.6 to 7.0] *6.3 to 6.9*.

36. The blood sample according to claim 33, characterized in that it is derived from human blood.

37. A blood withdrawing vessel *comprising*

*an evacuated chamber which is provided for receiving blood* containing a nucleic acid-stabilizing aqueous solution for stabilizing nucleic acids in [the withdrawn] blood directly upon contact with the solution,

*wherein* the solution [comprising] *comprises* the following components:

a guanidinium salt in a concentration of 1 to 8.0 M;

a buffer substance in a concentration of 10 to 300 mM;

a detergent in a concentration of 5 to 30%, by wt.

38. The vessel according to claim 37, characterized in that the guanidinium salt is selected from guanidinium thiocyanate and guanidinium chloride.

39. The vessel according to claim 38, characterized in that the guanidinium salt is present at a concentration of 2.5 to 8.0 M.

40. The vessel according to claim 37, characterized in that the detergent is selected from Triton-X-100, NP-40, polydocanol and Tween 20.

41. The vessel according to claim 37, characterized in that the buffer substance is selected from Tris, HEPES, MOPS, citrate and phosphate buffer.

42. The vessel according to claim 37, [characterized in that the] *further comprising a reducing agent, wherein said* reducing agent is *a material* selected from *the group consisting of* dithiothreitol, β-mercaptoethanol and TCEP.

43. The vessel according to claim 37, characterized in that the pH of the solution is between 4.0 and 7.5.

44. The vessel according to claim 43, characterized in that the pH of the solution is between [4.0] *5.0* and 6.5.

[45. The vessel according to claim 37, characterized in that it has a vacuum in the chamber which is provided for receiving blood.]

46. The vessel according to claim 37, characterized in that it contains withdrawn blood.

47. A method of withdrawing blood, comprising the step of directly introducing the blood into a vessel according to claim 37.

48. The method according to claim 47, characterized in that an amount of blood is withdrawn that is 0.1 to 4 times the volume of the solution in the vessel.

49. The method according to claim 48, characterized in that the final concentration of the guanidinium salt after blood supply is between 1.0 M and 5 M.

50. The method according to claim 48, characterized in that the final concentration of the guanidinium salt after blood supply is between 1.5 M and 5 M.

51. The method according to claim [37] *47*, characterized in that the pH of *the resultant mixture of* solution [is adjusted such that, following the addition of the sample material, a pH between 4.0 and 7.5 is obtained] *and blood is between 5.0 and 7.6*.

52. A method for stabilizing and/or isolating nucleic acids from blood, comprising the step of introducing blood into a vessel according to claim 37 and, optionally, isolating the nucleic acids with conventional methods.

53. A stabilized blood sample obtainable by [intro ducing] *introducing* whole blood into a vessel according to claim 37.

54. The blood sample according to claim 53, characterized in that it has a pH of [4.0 to 7.5] *5.0 to 7.6*.

55. The blood sample according to claim 53, characterized in that it has a pH of [6.6 to 7.0] *6.3 to 6.9*.

56. The blood sample according to claim 53, characterized in that it is derived from human blood.

*57. A process for collecting and stabilizing a blood sample, the process comprising:*

*providing a vessel comprising an interior, the interior comprising an aqueous solution that comprises a guanidinium salt, a buffer, a reducing agent and a detergent; and*

*drawing the blood sample from a blood vessel directly into the interior, wherein the aqueous solution causes lysis of cells in the blood and stabilizes nucleic acids in the sample.*

*58. The process of claim 57, wherein the interior is evacuated and wherein the evacuation is used to draw the blood sample.*

*59. The process of claim 58, wherein the vessel comprises a tube having an open end sealed by a septum.*

*60. The process of claim 58, wherein the evacuation is effective for drawing a specific volume of the blood into the interior.*

*61. The process of claim 57, wherein the guanidinium salt, the buffer, the reducing agent and the detergent are present in amounts effective to provide cell lysis and stabilization of nucleic acids in the sample by inactivation of nucleases.*

*62. The process of claim 57, wherein the buffer is effective, upon drawing the blood into the interior, to provide the resultant mixture with a pH of 5.0 to 7.6.*

*63. The process of claim 62, wherein the buffer is effective, upon drawing the blood into the interior, to provide the resultant mixture with a pH of 6.3 to 6.9.*

*64. The process of claim 60, wherein the specific volume is about 0.1 to about 4 times the volume of the solution.*

*65. The process of claim 57, wherein the guanidinium salt is one or more salts selected from the group consisting of guanidinium thiocyanate and guanidinium chloride.*

*66. The process of claim 57, wherein the buffer is selected from the group consisting of: Tris (tris(hydroxymethyl)aminomethane), HEPES (4-(2-hydroxyethyl)-1-piperazineethanesulfonic acid), MOPS (4-morpholinepropanesulfonic acid), MES (4-morpholineethanesufonic acid), citrate and phosphate buffer.*

*67. The process of claim 57, wherein the reducing agent is selected from the group consisting of: DTT (dithiothreitol), β-mercaptoethanol and TCEP (tris(2-carboxyethyl)phosphine).*

*68. The process of claim 57, wherein the detergent is selected from the group consisting of: (polyethylene glycol tert-octylphenyl ether), (polyethylene glycol 4-nonylphenyl ether), Polydocanol (dodecyl polyethylene glycol ether) and (polyethylene glycol sorbitan monolaurate).*

*69. The process of claim 57, wherein the pH of the aqueous solution in the vessel prior to the drawing step is 4.0 to 7.5.*

*70. The process of claim 69, wherein the pH of the aqueous solution in the vessel prior to the drawing step is 5 to 6.*

*71. The process of claim 57, wherein the solution comprises a single buffer, a single reducing agent and a single detergent.*

*72. The process of claim 57, wherein the aqueous solution consists essentially of the guanidinium salt, the buffer, the reducing agent and the detergent.*

*73. The process of claim 57, further comprising the step of isolating the nucleic acids after the drawing step.*

*74. The process of claim 73, wherein the isolating step is performed at least 3 days after the drawing step.*

*75. The process of claim 74, wherein the isolating step is performed at least 6 days after the drawing step.*

*76. The process of claim 75, wherein the isolating step is performed at least 8 days after the drawing step.*

*77. A vessel comprising an interior, the interior comprising an aqueous solution that comprises a guanidinium salt, a buffer, a reducing agent and a detergent, wherein the interior is evacuated, and wherein the aqueous solution is capable of lysing blood cells and stabilizing nucleic acids.*

*78. The vessel of claim 77, wherein the vessel comprises a tube having an open end sealed by a septum.*

*79. The vessel of claim 77, wherein the evacuation is effective for drawing a specific volume of a fluid sample into the interior.*

*80. The vessel of claim 77, wherein the guanidinium salt, the buffer, the reducing agent and the detergent are present in amounts effective to provide cell lysis and stabilization of nucleic acids in a fluid sample by inactivation of nucleases.*

*81. The vessel of claim 79, wherein the buffer is effective, upon mixing with the specific volume of a blood sample, to provide the resultant mixture with a pH of 5.0 to 7.6.*

*82. The vessel of claim 81, wherein the buffer is effective to provide the resultant mixture with a pH of 6.3 to 6.9.*

*83. The vessel of claim 77, wherein the pH of the aqueous solution in the vessel is 4.0 to 7.5.*

*84. The vessel of claim 83, wherein the pH is 5 to 6.*

*85. The vessel of claim 79, wherein the specific volume is about 0.1 to about 4 times the volume of the solution.*

*86. The vessel of claim 77, wherein the guanidinium salt is one or more salts selected from the group consisting of guanidinium thiocyanate and guanidinium chloride.*

*87. The vessel of claim 77, wherein the buffer is selected from the group consisting of: Tris (tris(hydroxymethyl)aminomethane), HEPES (4-(2-hydroxyethyl)-1-piperazineethanesulfonic acid), MOPS (4-morpholinepropanesulfonic acid), MES (4-morpholineethanesufonic acid), citrate and phosphate buffer.*

*88. The vessel of claim 77, wherein the reducing agent is selected from the group consisting of: DTT dithiothreitol, β-mercaptoethanol and TCEP (tris(2-carboxyethyl)phosphine).*

*89. The vessel of claim 77, wherein the detergent is selected from the group consisting of: (polyethylene glycol tert-octylphenyl ether), (polyethylene glycol 4-nonylphenyl ether), Polydocanol (dodecyl polyethylene glycol ether) and (polyethylene glycol sorbitan monolaurate).*

*90. The vessel of claim 77, wherein the solution comprises a single buffer, a single reducing agent and a single detergent.*

*91. The vessel of claim 77, wherein the aqueous solution consists essentially of the guanidinium salt, the buffer, the reducing agent and the detergent.*

*92. A process for collecting and stabilizing a blood sample, the process comprising:*

*providing a vessel comprising an interior, the interior comprising an aqueous solution that comprises a guanidinium salt, a buffer and a reducing agent; and*

*drawing the blood sample from a blood vessel directly into the interior, wherein the aqueous solution causes lysis of cells in the blood and stabilizes nucleic acids in the sample.*

*93. The process of claim 92, wherein the interior is evacuated and wherein the evacuation is used to draw the blood sample.*

*94. The process of claim 93, wherein the vessel comprises a tube having an open end sealed by a septum.*

*95. The process of claim 93, wherein the evacuation is effective for drawing a specific volume of the blood into the interior.*

*96. The process of claim 92, wherein the guanidinium salt, the buffer and the reducing agent are present in amounts effective to provide cell lysis and stabilization of nucleic acids in the sample by inactivation of nucleases.*

*97. The process of claim 92, wherein the buffer is effective, upon drawing the blood into the interior, to provide the resultant mixture with a pH of 5.0 to 7.6.*

*98. The process of claim 97, wherein the buffer is effective, upon drawing the blood into the interior, to provide the resultant mixture with a pH of 6.3 to 6.9.*

*99. The process of claim 95, wherein the specific volume is about 0.1 to about 4 times the volume of the solution.*

*100. The process of claim 92, wherein the guanidinium salt is one or more salts selected from the group consisting of guanidinium thiocyanate and guanidinium chloride.*

*101. The process of claim 92, wherein the buffer is selected from the group consisting of: Tris (tris(hydroxymethyl)aminomethane), HEPES (4-(2-hydroxyethyl)-1-piperazineethanesulfonic acid), MOPS (4-morpholinepropanesulfonic acid), MES (4-morpholineethanesufonic acid), citrate and phosphate buffer.*

*102. The process of claim 92, wherein the reducing agent is selected from the group consisting of: DTT (dithiothreitol), β-mercaptoethanol and TCEP (tris(2-carboxyethyl)phosphine).*

*103. The process of claim 92, wherein the pH of the aqueous solution in the vessel prior to the drawing step is 4.0 to 7.5.*

*104. The process of claim 103, wherein the pH of the aqueous solution in the vessel prior to the drawing step is 5 to 6.*

*105. The process of claim 92, further comprising the step of engaging the vessel with a blood sampling accessory.*

*106. The process of claim 92, wherein the solution comprises a single buffer and a single reducing agent.*

*107. The process of claim 92, wherein the aqueous solution consists essentially of the guanidinium salt, the buffer and the reducing agent.*

*108. The process of claim 92, further comprising the step of isolating the nucleic acids after the drawing step.*

*109. The process of claim 108, wherein the isolating step is performed at least 3 days after the drawing step.*

*110. The process of claim 109, wherein the isolating step is performed at least 6 days after the drawing step.*

*111. The process of claim 110, wherein the isolating step is performed at least 8 days after the drawing step.*

*112. A vessel comprising an interior, the interior comprising an aqueous solution that comprises a guanidinium salt, a buffer, and a reducing agent, wherein the interior is evacuated, and wherein the aqueous solution is capable of lysing blood cells and stabilizing nucleic acids.*

*113. The vessel of claim 112, wherein the vessel comprises a tube having an open end sealed by a septum.*

*114. The vessel of claim 112, wherein the evacuation is effective for drawing a specific volume of a fluid sample into the interior.*

*115. The vessel of claim 112 wherein the guanidinium salt, the buffer and the reducing agent are present in amounts effective to provide cell lysis and stabilization of nucleic acids in a fluid sample by inactivation of nucleases.*

*116. The vessel of claim 114, wherein the buffer is effective, upon mixing with the specific volume of a blood sample, to provide the resultant mixture with a pH of 5.0 to 7.6.*

*117. The vessel of claim 116, wherein the buffer is effective to provide the resultant mixture with a pH of 6.3 to 6.9.*

*118. The vessel of claim 112, wherein the pH of the aqueous solution in the vessel is 4.0 to 7.5.*

*119. The vessel of claim 118, wherein the pH is 5 to 6.*

*120. The vessel of claim 114, wherein the specific volume is about 0.1 to about 4 times the volume of the solution.*

*121. The vessel of claim 112, wherein the guanidinium salt is one or more salts selected from the group consisting of guanidinium thiocyanate and guanidinium chloride.*

*122. The vessel of claim 112, wherein the buffer is selected from the group consisting of: Tris (tris(hydroxymethyl)aminomethane), HEPES (4-(2-hydroxyethyl)-1-piperazineethanesulfonic acid), MOPS (4-morpholinepropanesulfonic acid), MES (4-morpholineethanesufonic acid), citrate and phosphate buffer.*

*123. The vessel of claim 112, wherein the reducing agent is selected from the group consisting of: DTT (dithiothreitol), β-mercaptoethanol and TCEP (tris(2-carboxyethyl)phosphine).*

*124. The vessel of claim 112, wherein the solution comprises a single buffer and a single reducing agent.*

*125. The vessel of claim 112, wherein the aqueous solution consists essentially of the guanidinium salt, the buffer and the reducing agent.*

*126. A process for collecting and stabilizing a blood sample, the process comprising:*

*providing a vessel comprising an interior, the interior comprising an aqueous solution that comprises a guanidinium salt, a buffer and a detergent; and*

*drawing the blood sample from a blood vessel directly into the interior, wherein the aqueous solution causes lysis of cells in the blood and stabilizes nucleic acids in the sample.*

*127. The process of claim 126, wherein the interior is evacuated and wherein the evacuation is used to draw the blood sample.*

*128. The process of claim 127, wherein the vessel comprises a tube having an open end sealed by a septum.*

*129. The process of claim 127, wherein the evacuation is effective for drawing a specific volume of the blood into the vessel.*

*130. The process of claim 126, wherein the guanidinium salt, the buffer and the detergent are present in amounts effective to provide cell lysis and stabilization of nucleic acids in the sample by inactivation of nucleases.*

*131. The process of claim 126, wherein the buffer is effective, upon drawing the blood into the interior, to provide the resultant mixture with a pH of 5.0 to 7.6.*

*132. The process of claim 131, wherein the buffer is effective, upon drawing the blood into the interior, to provide the resultant mixture with a pH of 6.3 to 6.9.*

*133. The process of claim 129, wherein the specific volume is about 0.1 to about 4 times the volume of the solution.*

*134. The process of claim 126, wherein the guanidinium salt is one or more salts selected from the group consisting of guanidinium thiocyanate and guanidinium chloride.*

*135. The process of claim 126, wherein the buffer is selected from the group consisting of: Tris (tris(hydroxymethyl)aminomethane), HEPES (4-(2-hydroxyethyl)-1-piperazineethanesulfonic acid), MOPS (4-morpholinepropanesulfonic acid), MES (4-morpholineethanesufonic acid), citrate and phosphate buffer.*

*136. The process of claim 126, wherein the one detergent is selected from the group consisting of: (polyethylene glycol tert-octylphenyl ether), (polyethylene glycol 4-nonylphenyl ether), Polydocanol (dodecyl polyethylene glycol ether) and (polyethylene glycol sorbitan monolaurate).*

*137. The process of claim 126, wherein the pH of the aqueous solution in the vessel prior to the drawing step is 4.0 to 7.5.*

*138. The process of claim 137 wherein the pH of the aqueous solution in the vessel prior to the drawing step is 5 to 6.*

*139. The process of claim 126, wherein the solution comprises a single buffer and a single detergent.*

*140. The process of claim 126, wherein the aqueous solution consists essentially of the guanidinium salt, the buffer and the detergent.*

*141. The process of claim 126, further comprising the step of isolating the nucleic acids after the drawing step.*

*142. The process of claim 141, wherein the isolating step is performed at least 3 days after the drawing step.*

*143. The process of claim 142, wherein the isolating step is performed at least 6 days after the drawing step.*

*144. The process of claim 143, wherein the isolating step is performed at least 8 days after the drawing step.*

*145. A vessel comprising an interior, the interior comprising an aqueous solution that comprises a guanidinium salt, a buffer and a detergent, wherein the interior is evacuated, and wherein the aqueous solution is capable of lysing blood cells and stabilizing nucleic acids.*

*146. The vessel of claim 145, wherein the vessel comprises a tube having an open end sealed by a septum.*

*147. The vessel of claim 145, wherein the evacuation is effective for drawing a specific volume of a fluid sample into the interior.*

*148. The vessel of claim 145, wherein the guanidinium salt, the buffer and the detergent are present in amounts effective to provide cell lysis and stabilization of nucleic acids in a fluid sample by inactivation of nucleases.*

*149. The vessel of claim 147, wherein the buffer is effective, upon mixing with the specific volume of a blood sample, to provide the resultant mixture with a pH of 5.0 to 7.6.*

*150. The vessel of claim 149, wherein the buffer is effective to provide the resultant mixture with a pH of 6.3 to 6.9.*

*151. The vessel of claim 145, wherein the pH of the aqueous solution in the vessel is 4.0 to 7.5.*

*152. The vessel of claim 151, wherein the pH is 5 to 6.*

*153. The vessel of claim 147, wherein the specific volume is about 0.1 to about 4 times the volume of the solution.*

*154. The vessel of claim 145, wherein the guanidinium salt is one or more salts selected from the group consisting of guanidinium thiocyanate and guanidinium chloride.*

*155. The vessel of claim 145, wherein the buffer is selected from the group consisting of: Tris (tris(hydroxymethyl)aminomethane), HEPES (4-(2-hydroxyethyl)-1-piperazineethanesulfonic acid), MOPS (4-morpholinepropanesulfonic acid), MES (4-morpholineethanesufonic acid), citrate and phosphate buffer.*

*156. The vessel of claim 145, wherein the detergent is selected from the group consisting of: (polyethylene glycol tert-octylphenyl ether), (polyethylene glycol 4-nonylphenyl ether), Polydocanol (dodecyl polyethylene glycol ether) and (polyethylene glycol sorbitan monolaurate).*

*157. The vessel of claim 145, wherein the solution comprises a single buffer and a single detergent.*

*158. The vessel of claim 145, wherein the aqueous solution consists essentially of the guanidinium salt, the buffer and the detergent.*

* * * * *